US007761136B2

(12) United States Patent
Ohishi et al.

(10) Patent No.: US 7,761,136 B2
(45) Date of Patent: Jul. 20, 2010

(54) MEDICAL IMAGE PROCESSING APPARATUS FOR SCANNING BASED ON A SET THREE-DIMENSIONAL REGION OF INTEREST

(75) Inventors: Satoru Ohishi, Otawara (JP); Kunio Aoki, Yaita (JP)

(73) Assignee: Kabushiki Kaisha Toshiba, Kawasaki-shi (JP)

( * ) Notice: Subject to any disclaimer, the term of this patent is extended or adjusted under 35 U.S.C. 154(b) by 329 days.

(21) Appl. No.: 11/292,355

(22) Filed: Dec. 2, 2005

(65) Prior Publication Data

US 2006/0082598 A1    Apr. 20, 2006

Related U.S. Application Data

(60) Continuation of application No. 10/162,646, filed on Jun. 6, 2002, now abandoned, which is a division of application No. 09/488,673, filed on Jan. 21, 2000, now Pat. No. 6,721,590.

(30) Foreign Application Priority Data

Jan. 21, 1999   (JP)   ............................ 11-013470

(51) Int. Cl.
*A61B 5/05*   (2006.01)
(52) U.S. Cl. .................. 600/425; 600/427; 600/431; 378/16; 378/20; 378/62; 378/150
(58) Field of Classification Search ................. 600/411, 600/420, 425, 427, 431, 437; 382/130–132; 378/151, 157, 205
See application file for complete search history.

(56) References Cited

U.S. PATENT DOCUMENTS 5,160,847 A * 11/1992 Leavitt et al. ............ 250/505.1
5,386,450 A * 1/1995 Ozawa ...................... 378/98.2
5,490,197 A    2/1996 Albert et al.
5,633,951 A    5/1997 Moshfeghi
5,647,360 A    7/1997 Bani-Hashemi et al.
5,690,106 A    11/1997 Bani-Hashemi et al.
5,745,548 A    4/1998 Dobbs et al.
5,754,623 A    5/1998 Seki (Continued)

FOREIGN PATENT DOCUMENTS

JP   08-280657   10/1996

(Continued)

*Primary Examiner*—Brian Casler
*Assistant Examiner*—Parikha S Mehta
(74) *Attorney, Agent, or Firm*—Oblon, Spivak, McClelland, Maier & Neustadt, L.L.P.

(57) ABSTRACT

In a storing unit of a medical image processing apparatus, first 3D image corresponding to a first period and second 3D image data corresponding to a second period are stored. The first 3D image data corresponds to a period before contrast agent injection operation and/or therapeutic operation. The second 3D image data corresponds to a period after the contrast agent injection operation and/or therapeutic operation. A 3D subtracting unit subtracts the first 3D image data from the second 3D image data. In 3D subtraction image data, a portion having undergone a change due to contrast agent injection operation and/or therapeutic operation is emphasized. A pseudo 3D image data generating unit generates pseudo 3D image data on the basis of 3D subtraction image data. A displaying unit displays the pseudo 3D image data.

2 Claims, 10 Drawing Sheets

U.S. PATENT DOCUMENTS 5,848,121 A    12/1998   Gupta et al.
5,970,112 A    10/1999   Hsieh
6,075,836 A     6/2000   Ning
6,144,759 A    11/2000   Weese et al.
6,149,301 A *  11/2000   Kautzer et al. .............. 378/205
6,217,214 B1    4/2001   Cabral et al.
6,320,928 B1   11/2001   Vaillant et al.
6,501,828 B1   12/2002   Popescu

FOREIGN PATENT DOCUMENTS

WO      WO 99/01066       1/1999

* cited by examiner

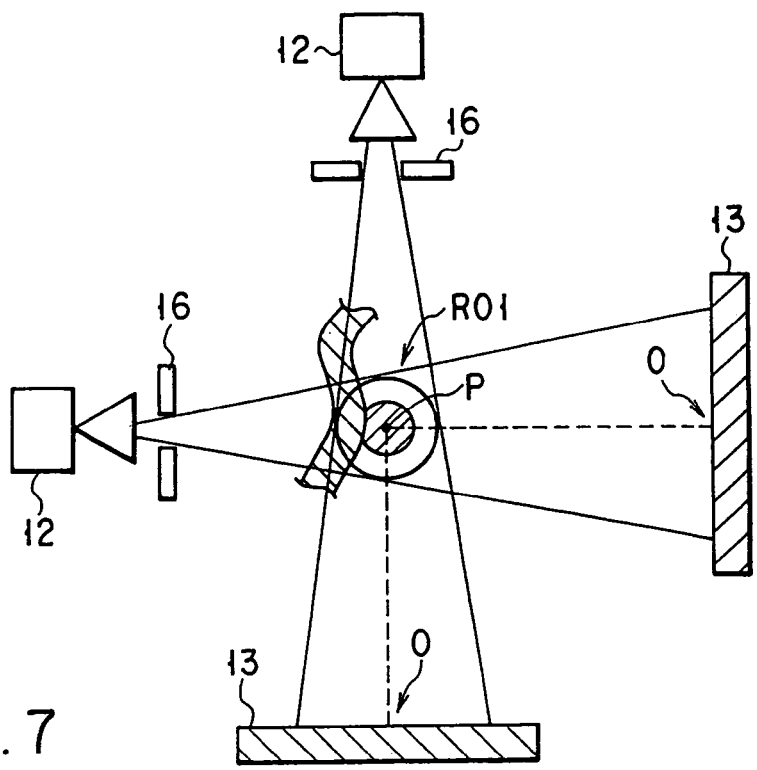
FIG. 7
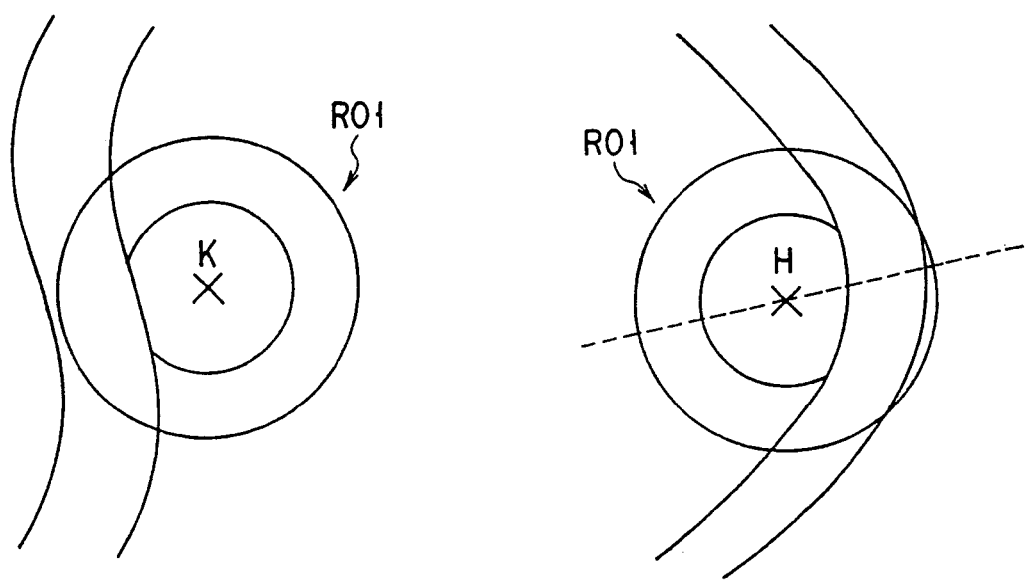
FRONTAL
FIG. 10A
LATERAL
FIG. 10B

MEDICAL IMAGE PROCESSING APPARATUS FOR SCANNING BASED ON A SET THREE-DIMENSIONAL REGION OF INTEREST

CROSS-REFERENCE TO RELATED APPLICATIONS

This application is a continuation application of, and claims priority to, U.S. application Ser. No. 10/162,646, filed Jun. 6, 2002, which claims priority to U.S. patent application Ser. No. 09/488,673, filed Jan. 21, 2000 (now U.S. Pat. No. 6,721,590), which claims priority from Japanese Application No. 11-013470, filed Jan. 21, 1999. The entire contents of each of the above applications and patents are incorporated herein by reference.

BACKGROUND OF THE INVENTION

The present invention relates to a medical image processing apparatus for supporting an examination, diagnosis, and therapy using a catheter and the like.

According to a conventional therapeutic method for aneurysms, an incision is surgically made in a patient's body to expose a morbid portion (aneurysm), and the neck of the exposed aneurysm is fastened with a clip to prevent blood from flowing into the aneurysm.

Recently, however, a great deal of attention has been given to a low-invasive therapeutic method represented by IVR (InterVentional Radiology). The low-invasive therapeutic method is also applied to a therapy for aneurysms. For example, a catheter is inserted into a patient's body from the groin to an aneurysm through a blood vessel. This operation is performed with a guide of a blood vessel image (to be referred to as a "contrast image" hereinafter) whose contrast is enhanced by a contrast agent. When the catheter reaches the aneurysm, a coil-like occlusive material 200 shown in FIG. 1 is injected from the distal end of the catheter into the aneurysm to fill the aneurysm with the occlusive material 200. The blood then stagnates in the aneurysm filled with the occlusive material 200. The stagnant blood coagulates after a while. With this operation, a therapeutic effect similar to that of a clip therapy can be obtained.

There are various occlusive materials 200 with different materials, shapes, sizes, and the like. Selecting the occlusive material 200 having a suitable size for the size of the internal portion of the aneurysm is important to attain a desired therapeutic effect. To three-dimensionally grasp the size of the internal portion of the aneurysm, a plurality of blood vessel extraction images acquired by DSM (Digital Subtraction Angiography) at a plurality of projection angles are used.

Such blood vessel extraction images are acquired after a surgical operation. A therapeutic effect is checked by comparing these blood vessel extraction images after the surgical operation with those acquired before the surgical operation. In general, to improve the precision of this therapeutic effect check, blood vessel extraction images are acquired after a surgical operation at the same projection angles as those before the surgical operation.

As described above, contrast images and blood vessel extraction images acquired at a plurality of projection angles are very effective in grasping the 3D structure of a target.

The power of expression of contrast images and blood vessel extraction images is not sufficient to grasp the complicated structure of a blood vessel. For this reason, it may take much time to move a catheter to a target. In addition, it may take much time to search for optimal projection angles, or radiography may need to be repeated many times at various projection angles to obtain detailed depth information.

Furthermore, blood vessel extraction images are acquired to check an occlusive material therapy and medical therapeutic effect in a catheter therapy. To perform this check, images of the aneurysm and nearby portions are required, but images of portions outside them are not required. In this case, X-rays with which these outside portions are irradiated will cause unnecessary exposure to X-rays.

BRIEF SUMMARY OF THE INVENTION

It is an object of the present invention to provide an image which effectively supports an operator in grasping the 3D structure of a blood vessel in a medical image processing apparatus.

According to the present invention, in a medical image processing apparatus, a storing unit stores first 3D image data corresponding to a first period and second 3D image data corresponding to a second period. The first 3D image data corresponds a period before condition changing. The second 3D image data corresponds to a period after condition changing. A 3D subtracting unit subtracts the first 3D image data from the second 3D image data. In 3D subtraction image data, a portion that has changed due to the condition changing is emphasized. The pseudo 3D image data generating unit generates pseudo 3D image data on the basis of the 3D subtraction image data. A display unit displays pseudo 3D image data.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 7 is a view showing a rotational center aligned with the center of an ROI in the first modification of this embodiment;

FIG. 10A is a view for supplementing the description of ROI setting in FIG. 9;

FIG. 10B is a view for supplementing the description of ROI setting in FIG. 9;

DETAILED DESCRIPTION OF THE INVENTION

An image processing display apparatus according to each embodiment of the present invention will be described below with reference to the views of the accompanying drawing. The image processing display apparatus according to the present invention includes a modality capable of acquiring 3D images, e.g., an X-ray diagnosis apparatus, ultrasonic diagnosis apparatus, X-ray computer tomography apparatus (X-ray CT), magnetic resonance imaging apparatus (MRI), or nuclear magnetic diagnosis apparatus (SPECT, PET). Recently, 3D (three dimensional) image is obtain used for diagnosing and treating. In this case, 3D images having various information are generated. For example, an X-ray diagnosis apparatus, and more specifically, an X-ray diagnosis apparatus for the circulatory system, will be described below as an image processing display apparatus.

First Embodiment

Figure 2:
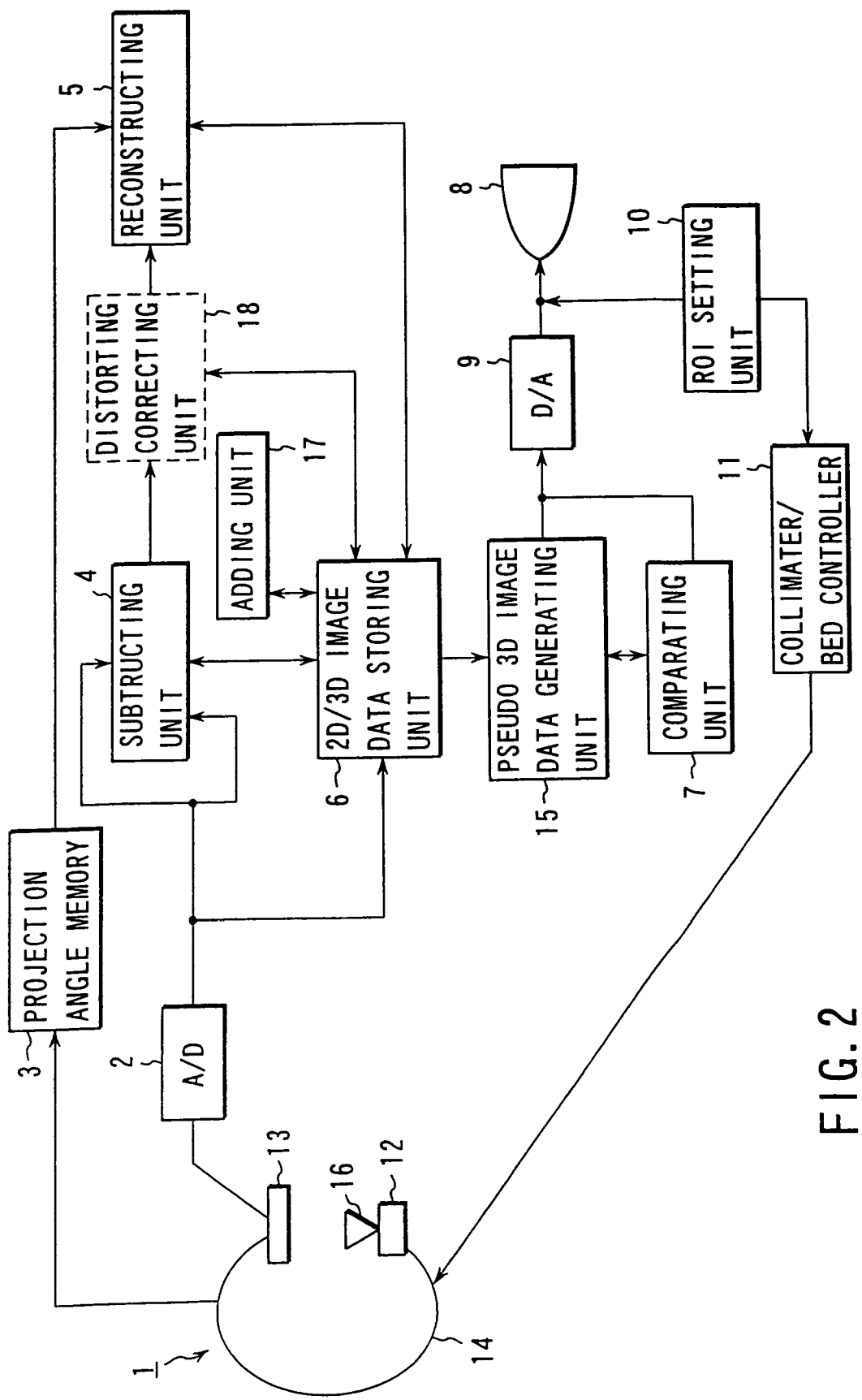
FIG. 2 is a block diagram showing the arrangement of an X-ray diagnosis apparatus for the circulatory system according to the first embodiment of the present invention.

As shown in FIG. 2, the X-ray diagnosis apparatus according to the first embodiment has a radiography unit 1. The radiography unit 1 includes an arcuated arm 14 capable of rotating about three axes including the body axis of a subject, an X-ray tube 12 mounted on one end of the arcuated arm 14, an X-ray collimator 16 mounted in the X-ray window of the X-ray tube 12, and a camera system 13 mounted on the other end of the arcuated arm 14. For the sake of descriptive convenience, a rotational angle about the body axis of the subject corresponds to a projection angle. This projection angle data is stored in a projection angle memory 3. The camera system 13 is comprised of an image intensifier, optical system, and TV camera. The camera system 13 may be a planar X-ray detector constituted by solid image sensing elements, each having a scintillator and photodiode, arrayed in the form of a matrix.

An A/D converter 2 converts an analog video signal output from the camera system 13 into a digital signal. A 2D/3D image data storing unit 6 is configured to store 2D and 3D image data to be processed in this system, including this converted 2D image data (original 2D image data).

A subtracting unit 4, adding unit 17, reconstructing unit 5, and distortion correcting unit 18 are mutually connected to the 2D/3D image data storing unit 6. The reconstructing unit 5 is configured to reconstruct 3D image data from multiangle 2D image data (original 2D image data or 2D subtraction image data) stored in the 2D/3D image data storing unit 6. This 3D image data may be binary data or gray-level data. For image reconstruction processing, for example, the weight correcting filtered-back projection method proposed by Feldkamp et al. is used.

The subtracting unit 4 is configured to subtract two 2D image data (original 2D image data or 2D subtraction image data) stored in the 2D/3D image data storing unit 6 or subtract two 3D image data stored in the 2D/3D image data storing unit 6. The adding unit 17 is configured to add two 3D image data stored in the 2D/3D image data storing unit 6. Note that target image data to be subjected to reconstruction processing, subtraction processing, and addition processing can be arbitrarily selected from the image data stored in the 2D/3D image data storing unit 6 in accordance with a user instruction.

A pseudo 3D image data generating unit 15 is configured to generate pseudo 3D image data such as surface image and projection image data for stereoscopically displaying a target on a 2D screen from 3D image data stored in the 2D/3D image data storing unit 6. A comparing unit 7 is configured to unify display parameters such as luminance to allow two or more pseudo 3D image data to be easily compared with each other. The image data generated by these units 15 and 7 are sent to a displaying unit 8 through a D/A converter 9.

A ROI setting unit 10 is configured to allow the operator to set a region of interest (ROI) on the image displayed on the displaying unit 8. A collimater/bed controller 11 adjusts the aperture of the X-ray collimator 16 and changes the position of the bed in accordance with the set region of interest.

The operation of the first embodiment will be described next.

Figure 3:
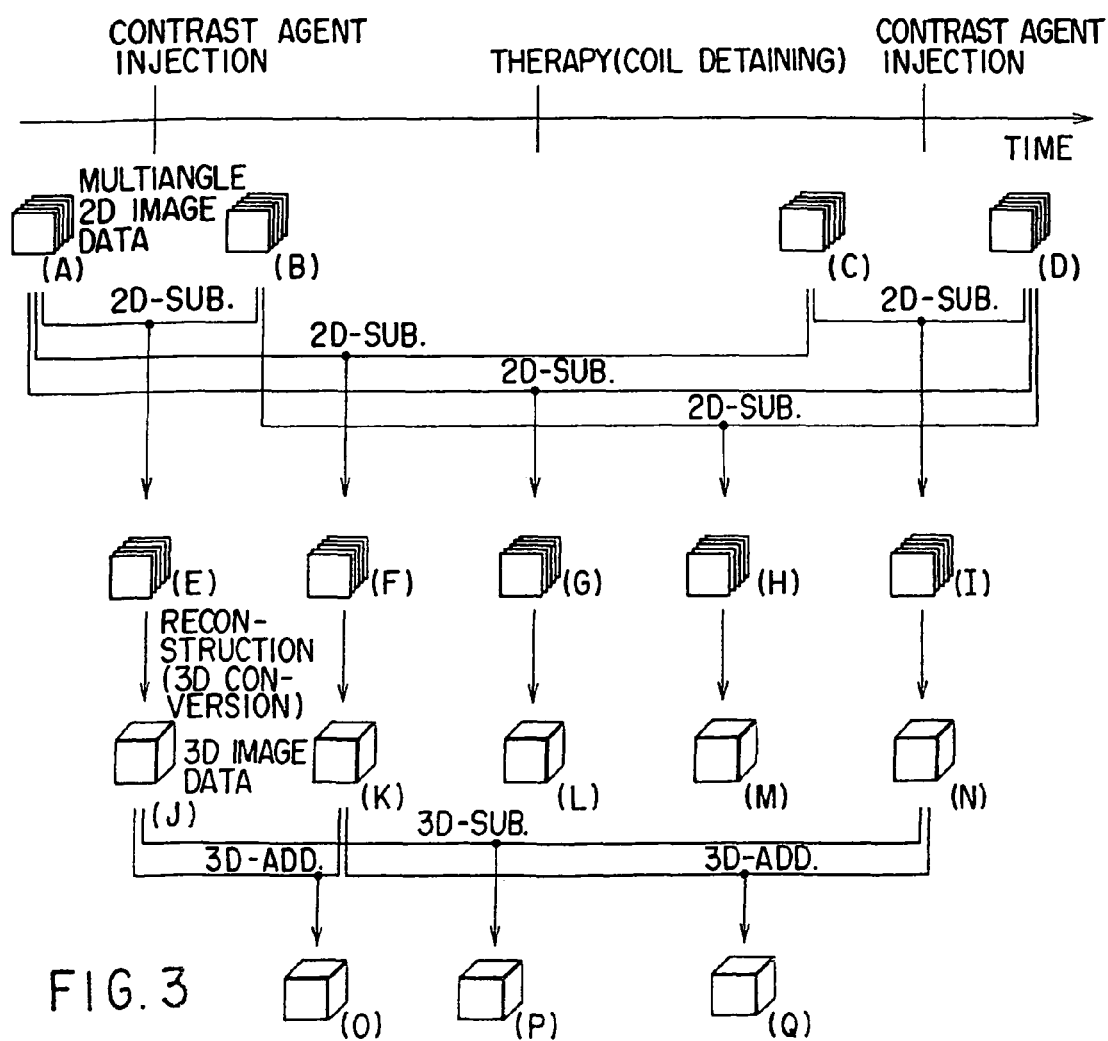
FIG. 3 is a view showing a plurality of types of images that can be generated in this embodiment and procedures for processing the images.

FIG. 3 shows the temporal relationship between various events and radiographic operation. FIG. 3 shows various 2D and 3D image data that can be generated, together with the flow of corresponding processes (subtraction processes, addition processes, and reconstruction processes).

Figure 1:
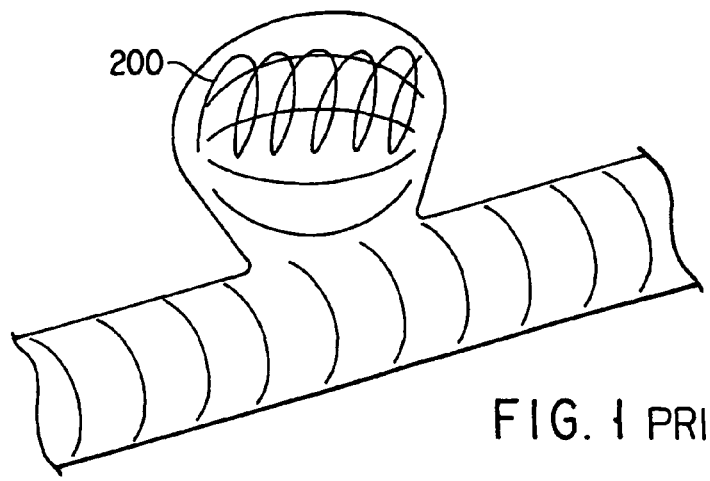
FIG. 1 a schematic view showing an occlusive material (coil) detained in an aneurysm to perform therapy for the aneurysm.

As events, the therapeutic operation for an aneurysm in FIG. 1 and contrast agent injection operation are assumed. At least two radiographic operations are performed before the therapeutic operation. One radiographic operation is performed before a contrast agent injection operation. The other radiographic operation is performed after the contrast agent injection operation. Original multiangle 2D image data (A, B) that can be used for reconstruction processing of 3D image data are acquired by the two radiographic operations. Each multiangle 2D image data includes, for example, 120 images acquired at projection angle intervals of 3°.

Similarly, at least two radiographic operations are performed after the therapeutic operation. One radiographic operation is performed before a contrast agent injection operation. The other radiographic operation is performed after the contrast agent injection operation. Original multiangle 2D image data (C, D) that can be used for reconstruction processing of 3D image data are acquired by the two radiographic operations. The multiangle 2D image data (A, B, C, D) are stored in the 2D/3D image data storing unit 6.

The subtracting unit 4 subtracts 2D image data (A) before contrast agent injection from 2D image data (B) after contrast agent injection in units of projection angles to obtain multiangle 2D subtraction image data (E) before a therapy. This 2D image data (E) is stored in the 2D/3D image data storing unit 6. In this 2D image data (E), a blood vessel and an aneurysm before a therapy are emphasized.

The subtracting unit 4 subtracts 2D image data (C) before contrast agent injection from 2D image data (D) after contrast agent injection in units of projection angles to obtain multiangle 2D subtraction image data (I) after the therapy. This 2D image data (I) is stored in the 2D/3D image data storing unit 6. In this 2D image data (I), the blood vessel and the aneurysm after the therapy are emphasized.

The subtracting unit 4 subtracts the multiangle 2D image data (A) before the therapy and contrast agent injection from the multiangle 2D image data (C) after the therapy and contrast agent injection in units of projection angles to obtain multiangle 2D subtraction image data (F). This 2D image data (F) is stored in the 2D/3D image data storing unit 6. In the 2D image data (F), a coil detained in the aneurysm by the therapeutic operation is emphasized.

The subtracting unit 4 subtracts the multiangle 2D image data (D) before the therapy and contrast agent injection from the multiangle 2D image data (D) in units of projection angles to obtain multiangle 2D subtraction image data (G). This 2D image data (G) is stored in the 2D/3D image data storing unit 6. In this 2D image data (G), the blood vessel, aneurysm after the therapy, and coil detained in the aneurysm are emphasized.

The subtracting unit 4 subtracts the multiangle 2D image data (B) before the therapy and-after contrast agent injection from the multiangle 2D image data (D) after the therapy and contrast agent injection in units of projection angles to obtain multiangle 2D subtraction image data (H). This 2D image data (H) is stored in the 2D/3D image data storing unit 6. In the 2D image data (H), a changed portion between the aneurysm before the therapy and the aneurysm after the therapy is emphasized.

The reconstructing unit 5 converts the multiangle 2D subtraction image data (E, F, G, H, I) into 3D image data (J, K, L, M, N) by performing reconstruction processing and referring to the 3D image data using parameters such as the SID (the distance from the focal point of the X-ray tube 12 to the detector 13), radiographic mode, and projection angle which are stored in the projection angle memory 3. The 3D image data (J, K, L, M, N) are stored in the 2D/3D image data storing unit 6. Note that a reconstruction region is defined as a cylinder inscribed in an X-ray beam irradiated from the X-ray tube 12 in all directions. The internal portion of this cylinder must be divided into 3D discrete segments on the basis of a length d of a central portion of a reconstruction region projected on the width of one detection element of the detector 13, and a reconstructed image must be obtained from data of the discretion points. This discretion interval is an example and may change depending on the apparatus and maker. Basically, therefore, the discretion interval defined by each apparatus may be used. According to the Feldkamp method as a reconstruction method, for example, an appropriate convolution filter like the one used by Shepp & Logan or Ramachandran is applied to 120 2D images, and a 3D inverse projection computation is performed while multiplying the resultant data by a coefficient for correcting the 3D spread of a beam, thereby forming a 3D image.

The subtracting unit 4 subtracts 3D image data (N) from 3D image data. (J) to obtain 3D subtraction image data (P) that allows the operator to check a therapeutic effect.

The adding unit 17 adds 3D image data (K) to 3D image data (J) to acquire addition 3D image data (O) that allows the operator to check the state of the coil detained in the aneurysm by the therapeutic operation. If the operator recognizes from the addition 3D image data (O) the conditions of the coil and the aneurysm, he/she performs a therapeutic operation again.

The adding unit 17 adds the 3D image data (K) to the 3D image data (N) to acquire addition 3D image data (Q) that allows the operator to check the state of the coil detained in the aneurysm by the therapeutic operation. If the operator recognizes from the addition 3D image data (Q) the conditions of the coil and the aneurysm, he/she performs a therapeutic operation again.

Figure 4:
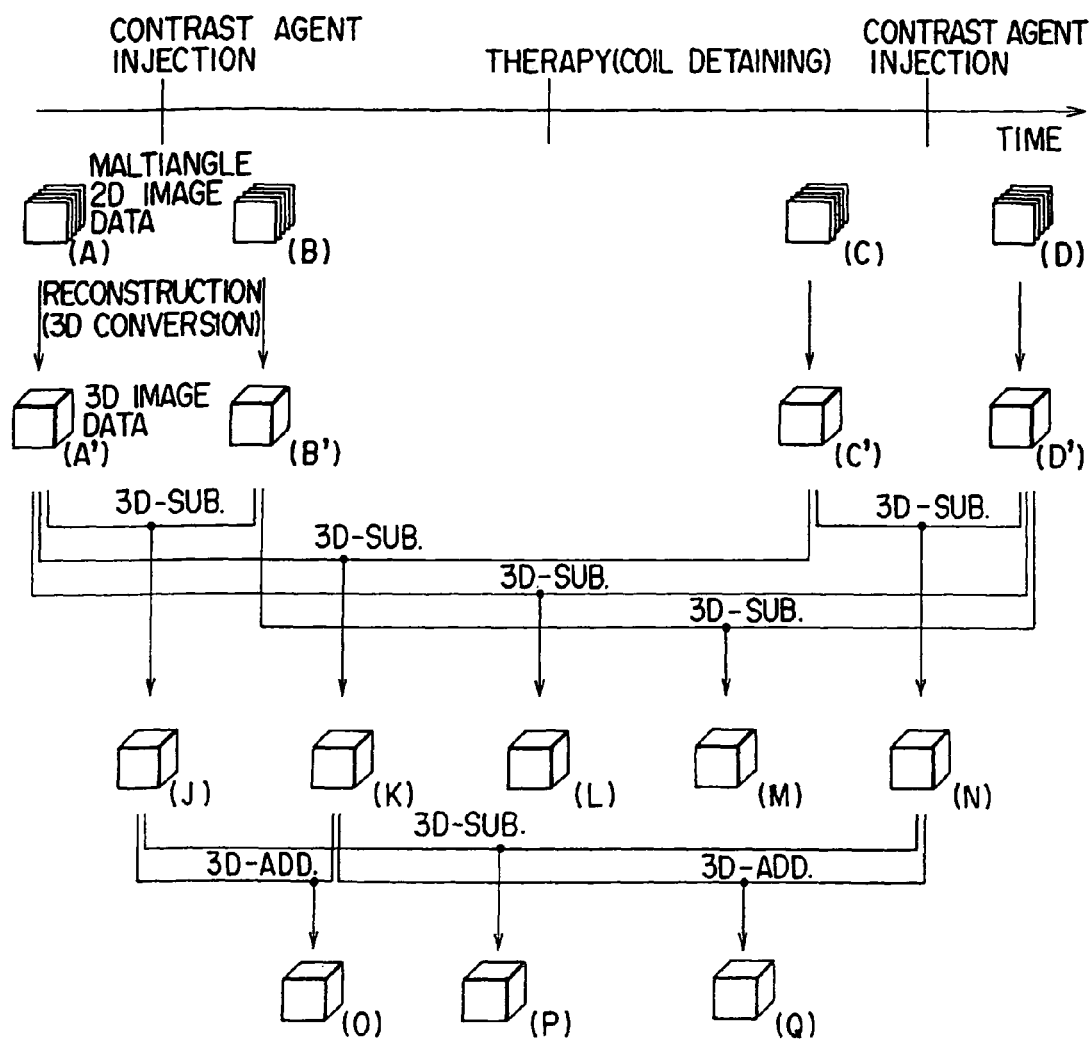
FIG. 4 is a view showing a plurality of types of images that can be generated in this embodiment and procedures for processing the images.

As shown in FIG. 4, the 3D image data (J, K, L, M, N) may be acquired by converting the multiangle original 2D image data (A, B, C, D) into 3D image data (A', B', C', D') by reconstruction processing, and performing 3D subtraction processing using 3D image data (A', B', C', D').

Various clinically useful 2D and 3D image data can be acquired by arbitrarily and selectively using reconstruction processing, 2D subtraction processing, 3D subtraction processing, 2D addition processing, and 3D addition processing in this manner.

The pseudo 3D image data generating unit 15 extracts the surface shapes of the blood vessel and aneurysm, by threshold processing, from the 3D image data (J to Q) selectively read out from the 2D/3D image data storing unit 6 in accordance with a user instruction, and performs shading on the basis of the surface shapes and depth information, thereby generating pseudo 3D image data (a 2D image looks like a 3D image) of the blood vessel and aneurysm observed from an arbitrary direction. This pseudo 3D image data is supplied to the displaying unit 8 through the D/A converter 9. As a consequence, a pseudo 3D image of the blood vessel and aneurysm observed from an arbitrary direction is displayed on the displaying unit 8.

In this case, surface rendering is used as a stereoscopic display method. However, the present invention is not limited to this, and other pseudo 3D image display methods such as volume rendering may be used.

A region of interest (ROI) including the aneurysm is set through the ROI setting unit 10 on the image of the blood vessel and aneurysm displayed on the displaying unit 8. For example, the ROI setting unit 10 is an input unit such as a mouse device, track ball, or keyboard. The ROI setting unit 10 is configured to set an ROI by designating the central position of the ROI and its radius.

More specifically, the operator designates a position regarded as the center of the aneurysm with the mouse device. A straight line expression is obtained from the designated position in a direction perpendicular to the image. A search for a 3D image is sequentially made on a pixel-width basis along this straight line, and a coordinate value A of a position at which a detected value exceeds the threshold first is stored. The search is continued to store a coordinate value B of a position at which a detected value becomes smaller than the threshold. The midpoint between the positions A and B is set as the center of the aneurysm.

A method of obtaining the center of an aneurysm is not limited to this method. For example, after a straight line expression is obtained from the position designated with the mouse device in a direction perpendicular to the image, similar processing is performed for an image observed at another angle, and the intersection of the obtained straight lines (in practice, the midpoint between points on the straight lines which approach most) may be obtained as the center of the aneurysm. In addition, the radius may be input with the keyboard, and a circle indicating the ROI, which is drawn on the image, may be enlarged/reduced with the mouse. In this case, the ROI is assumed to be a sphere. However, the ROI may have another shape. In addition, the display color of a portion in the ROI may be changed, or its display density may be inverted. Alternatively, a dot or stripe pattern may be pasted on the ROI. This facilitates recognition of the range of a set ROI. When the ROI is set in this manner, the ROI setting unit 10 supplies the ROI information (center and radius) to the collimater/bed controller 11.

Figure 5A:
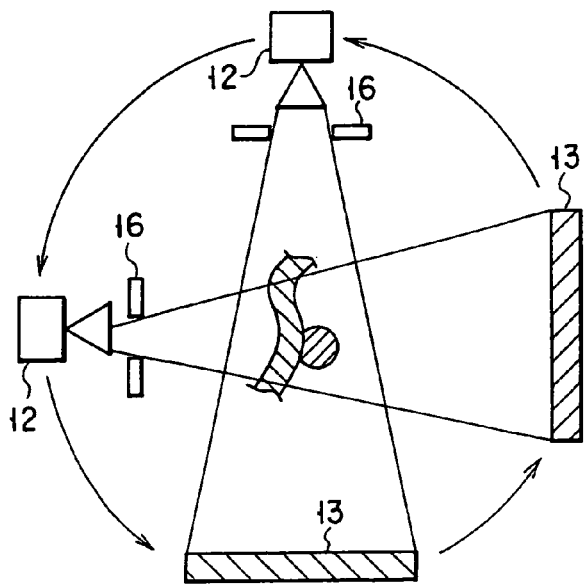
FIG. 5A is a view showing the maximum irradiation range in this embodiment.
Figure 5B:
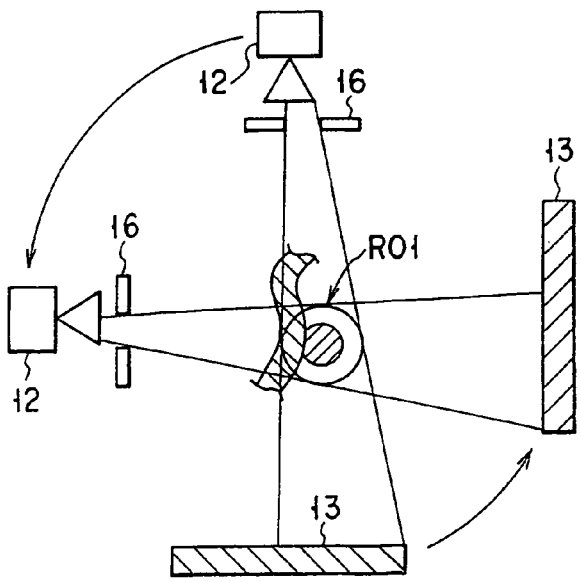
FIG. 5B is a view showing the reduced irradiation range in this embodiment.
Figure 6B:
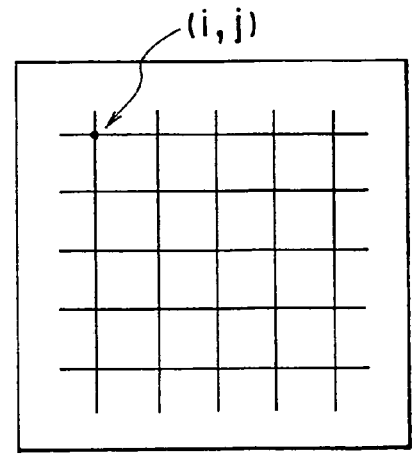
FIG. 6B is a schematic view showing a distortion-corrected image in this embodiment.

The collimater/bed controller 11 adjusts the aperture of the X-ray collimator 16 to irradiate only a region of the subject which corresponds to the ROI with X-rays at various projection angles on the basis of the information of the set ROI. Consider the case shown in FIGS. 5A and 5B. Before coil detaining, as shown in FIG. 5A, the aperture of the X-ray collimator 16 is widened to radiograph the overall blood vessel and aneurysm. When the ROI shown in FIG. 5B is set with the ROI setting unit 10, the aperture of the X-ray collimator 16 is narrowed to make an X-ray beam circumscribe the spherical ROI. The data indicating the aperture for each projection angle which is determined in this manner is used for multiangle radiographic operation (to be described below) after coil detaining.

Radiographic operation after coil detaining will be described next. After coil detaining, two sets of 120 2D images (C, D) are acquired at projection angle intervals of 3° by multiangle radiographic operation before contrast agent injection and multiangle radiographic operation after contrast agent injection. In this radiographic operation, the aperture is changed to irradiate only the ROI with X-rays on the basis of aperture data from the collimater/bed controller 11, and radiography is repeated, as shown in FIG. 5B. The image data obtained by this radiographic operation is A/D-converted, and the resultant data is stored in the 2D/3D image data storing unit 6.

The subtracting unit 4 subtracts each pair of images, of the images (C, D) acquired before/after contrast agent injection and stored in the 2D/3D image data storing unit 6, which are radiographed at the same projection angle from each other, and supplies the resultant subtraction image to the reconstructing unit 5. Subtraction processing is performed only within the projection region of the ROI. Other regions are handled as regions with no value. If, however, a blood vessel extends in a direction perpendicular to the rotational axis, and projection extends outside the ROI, a contrast-enhanced image value before coil detaining may be set outside the projection region of the ROI.

The first set of radiographic images supplied to the subtracting unit 4 includes contrast images (contrast-enhanced images) and mask images (non-contrast-enhanced images) before and after coil detaining. The reconstructing unit 5 form a 3D image of only the ROI on the basis of these subtraction images as in the above case. With this operation, an image (I) of the blood vessel and aneurysm with little blood is reconstructed. This image (I) is temporarily stored in the 2D/3D image data storing unit 6.

The next set of radiographic images supplied to the subtracting unit 4 includes mask images (C) after coil detaining and mask images (A) before coil detaining. The reconstructing unit 5 generates a 3D image of only the ROI on the basis of these subtraction images (G) as in the above case. With this operation, a 3D image (K) indicating the distribution of the coil (occlusive material) is generated. This 3D image (K) is also temporarily stored in the 2D/3D image data storing unit 6.

The operation of the comparing unit 7 will be described next. The comparing unit 7 unifies display parameters such as luminance to facilitate comparison between two or more pseudo 3D image data selected in accordance with a user instruction. The comparing unit 7 also arranges and displays two or more pseudo 3D image data with unified display parameters on one screen. Observing the arranged images, the observer can accurately grasp a change in blood flow before and after coil detaining, i.e., a therapeutic effect. Note that a plurality of pseudo 3D images may be displayed within the same area. This makes it possible to observe changes in the two images in a small display area. The pseudo 3D images may be simultaneously displayed in different colors. This makes it easier to recognize changes in the two images. In this case, overlapping portions of the pseudo 3D images may be simultaneously displayed or one of them may be preferentially displayed. This preferential image switching can be easily performed by designating with a user instruction.

When the pseudo 3D image data generating unit 15 is to generate a pseudo 3D image, not only information about a structure but also its density information may be simultaneously displayed. This makes it easier to recognize changes in the two images. If, for example, the information about the structure is displayed with luminance as before, and the density information is displayed in color, the two pieces of information can be grasped at once.

In addition, when at least two sets of pseudo 3D images generated by the pseudo 3D image data generating unit 15 are to be displayed, they may be rotated while being synchronized angularly. This allows the operator to observe the respective images at the same angles.

A case wherein a 3D image (J or N) and 3D image (L) are selected will be described next. The unit 15 generates pseudo 3D images observed from various directions on the basis of the 3D image (J or N) and 3D image (L), and supplies them to the comparing unit 7.

The adding unit 17 adds the 3D image (J or N) and 3D image (L) to obtain one image (O or Q), and supplies it to the displaying unit 8 through the D/A converter 9. At this time, the unit 15 uses the center coordinates of the ROI, which are obtained by the ROI setting unit 10 in advance, to obtain a plane that is perpendicular to the observation direction and passes through the center coordinates, and erases data located before the plane. This makes it possible to observe the state of the coil detained in the aneurysm from all directions, thus facilitating a check on the effect of the occluding operation and selection of an occlusive material to be detained in the aneurysm again.

Figure 6A:
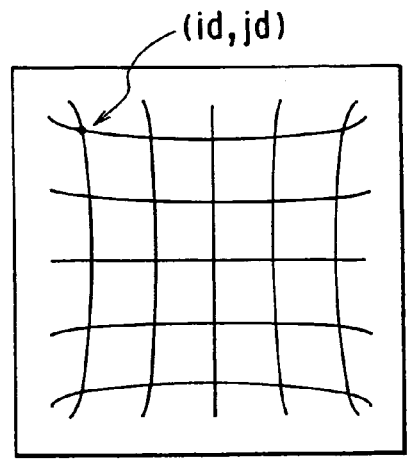
FIG. 6A is a schematic view showing a distorted image in this embodiment.

In this case, if the camera system 13 is made up of an image intensifier, optical system, and TV camera, 2D images distort. If a mesh pattern in the form of a square lattice is radiographed by the image intensifier, a distortion occurs, as shown in FIG. 6A. This is because, the I.I. has a spherical X-ray detection surface, and the detected image undergoes a pin-cushion distortion. In addition, the track of an electron beam bends due to the influence of magnetism such as geomagnetism, resulting in an s-shaped distortion. A corrected image corresponding to arbitrary position coordinates (id, jd) in FIG. 6A should be arranged at predetermined intervals two-dimensionally from the center. Assume that the corresponding position coordinates of the corrected image are (i, j). That is, (id, jd) and (i, j) respectively represent image coordinates on the acquired image and distortion-corrected image. The image coordinate system is a coordinate system having an upper left point on the image as an origin, an upper right point represented by (N−1, 0), an upper left point represented by (0, N−1), and a lower right point represented by (N−1, N−1). N represents the matrix size of the image. In general, N=512 or 1,204 [pixel]. The distortion of an I.I. image can be corrected by substituting the data of (i, j) on the corrected image for the data of (id, jd) on the acquired image.

The relationship between (i, j) and (id, jd) is determined by the location of the apparatus, projection angle, SID, and image intensifier size. This relationship slightly varies depending on the image intensifier to be used even if these conditions remain unchanged. The relationship between (i, j) and (id, jd) must therefore be grasped in advance under the respective conditions for each image intensifier to be used. In general, this relationship can be empirically obtained.

For example, a grid is bonded on the front surface of the image intensifier, and the grid is radiographed at each angle required for an examination to obtain the positions of grid points (intersections of wires) from the grid projection image. These grid points should be arranged at equal intervals two-dimensionally on the image if no distortion occurs. If, therefore, the grid points are rearranged, centered on the grid point nearest to the center of the image, at known inter-grid-point intervals, the image distortion is corrected. In addition, the positions of points other than the grid points can be approximately obtained on the basis of the positions of the surrounding grid points. The distortion correction unit performs such operation at each projection angle. With this distortion correcting unit 18, a displayed image without any distortion can be obtained even by using an image intensifier. This allows the operator to accurately observe a target therapy portion or the like.

First Modification of First Embodiment

After an ROI is set with the ROI setting unit 10, the controller 11 may control the bed and radiography unit 1 as well as the X-ray collimator 16 to move them to position a center P of the ROI to the center of the camera system 13 at all projection angles, as shown in FIG. 7. In this case, since the collimater 16 is controlled around the center O of the camera system 13 symmetrically in the vertical and horizontal directions, control of the collimater 16 can be facilitated.

Second Modification of First Embodiment

In the first embodiment, although an ROI is set on the basis of a 3D image, the amount of processing for reconstruction is enormous. Even if, for example, an apparatus designed specifically for reconstruction is used, it takes about six min to process 256×256×256 [pixel3]. It takes 384 min (6.4 hrs) or 3,072 min (51.2 hrs) to obtain a 3D image with a resolution of 1024×1024×1024 [pixel3] or 2048×2048×2048 [pixels] from image data acquired with a resolution of 1024×1024 [pixel2] or 2048×2048 [pixel2] by using an apparatus with the same reconstruction speed as that of the above apparatus. In addition, it takes 48 min to obtain a 3D image with a resolution of 512×512×512 [pixel3] even on the basis of acquired image data with a resolution of 512×512 [pixel2]. This reconstruction time is very long as compared with the time interval between the instant at which radiographic operation before coil detaining is complete and the instant at which multiangle radiographic operation is performed after the coil is detained. That is, this technique is not practical.

Figure 8:
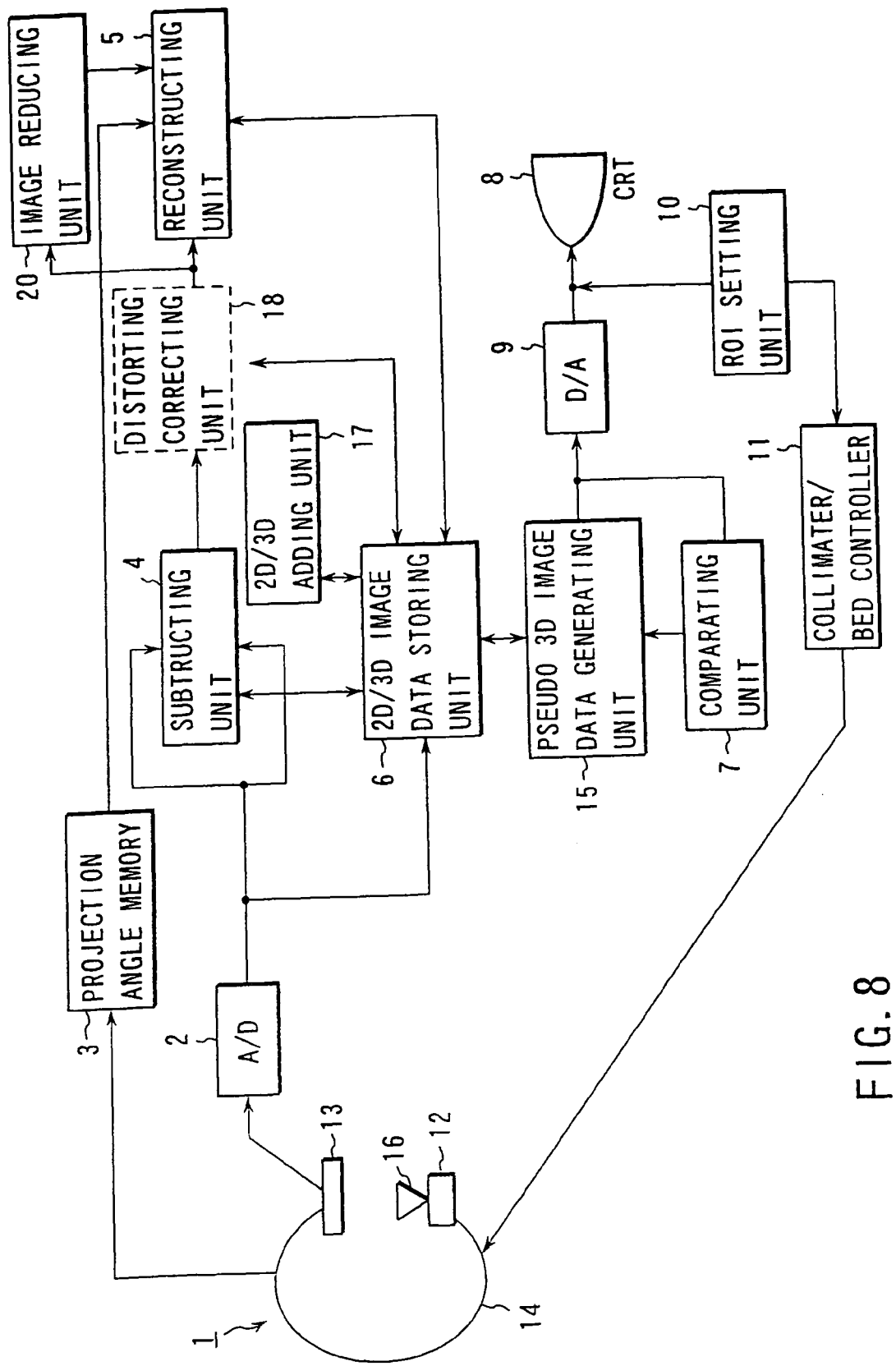
FIG. 8 is a block diagram showing a reduction processing unit provided to reduce the amount of 3D image generation processing for ROI setting in the second modification of this embodiment.

As shown in FIG. 8, therefore, an image reducing unit 20 is connected to the output stage of the subtracting unit 4, and a subtraction image (or a distortion-corrected image from the distortion correcting unit 18) is reduced in image reconstruction before coil detaining to perform reconstruction processing in the reconstructing unit 5 on the basis of the image reduced by this reduction processing. For example, image data of 1024×1024 [pixel2] is reduced to 256×256 [pixel2] or 128×128 [pixel2], and the reconstructing unit 5 performs image reconstruction processing on the basis of the reduced data.

This operation can greatly decrease the amount of processing to be performed by the X-ray diagnosis apparatus in the interval between the instant at which radiographic operation before coil-detaining is complete and the instant at which multiangle radiographic operation is performed again after an occlusive material is detained. The X-ray diagnosis apparatus can therefore finish setting an opening and bed position until the next multiangle radiographic operation.

Although the resolution of an image observed in ROI setting operation decreases due to this reduction processing, a 3D image formed from reduced image data is sufficient for this ROI setting operation because it is only required that the position and size of an aneurysm be approximately grasped. However, a 3D image (1) of only an ROI must be reconstructed again. This ROI image is preferably reconstructed immediately after ROI setting. At this time, it is preferable that the above reduction processing is not performed. Note that the above 3D image (N) and 3D image (P) are reconstructed after an occlusive material is detained and multiply operation radiographic operation is performed.

Third Modification of the First Embodiment

Figure 9:
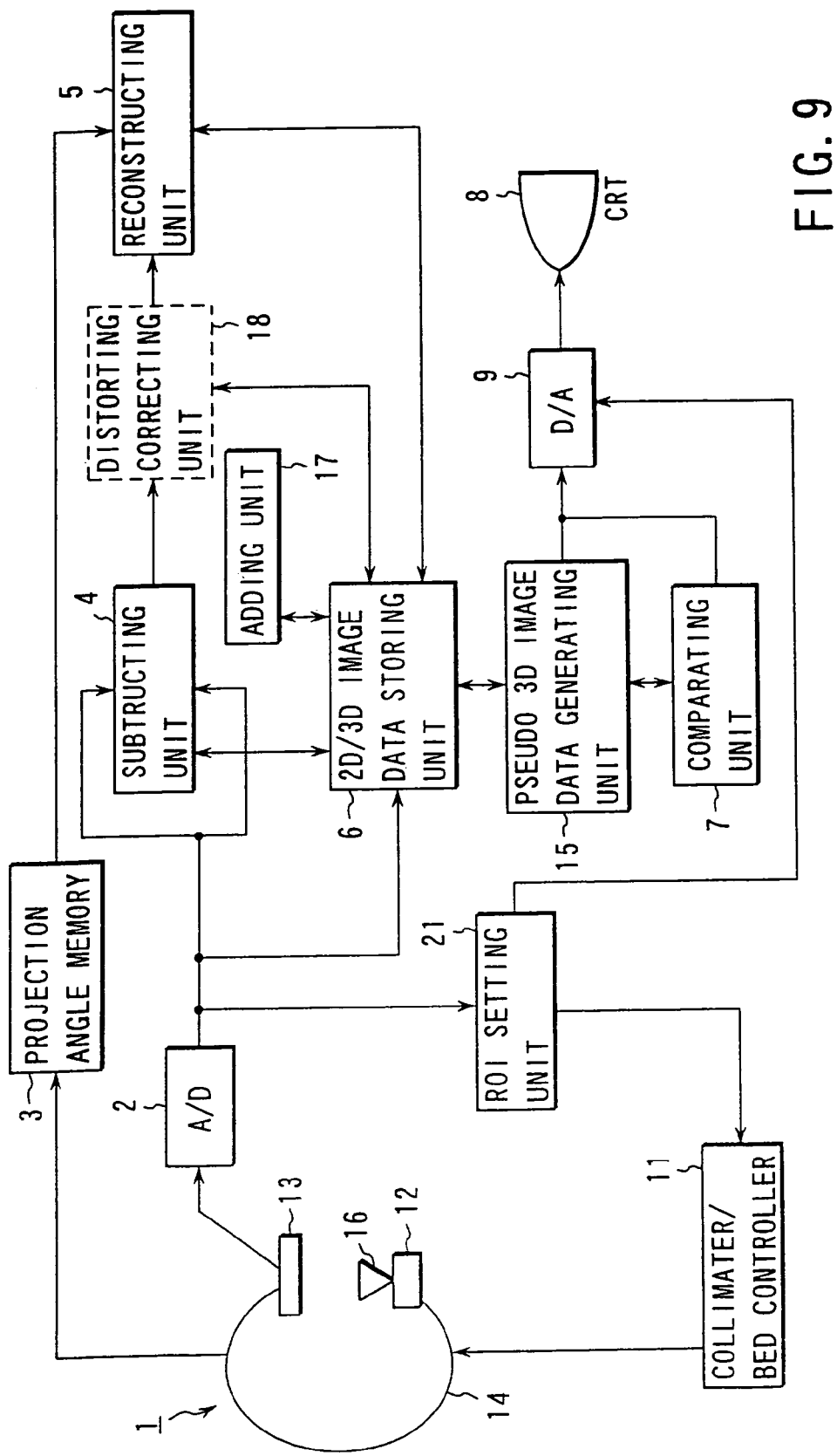
FIG. 9 is a block diagram showing an ROI setting unit for setting an ROI by using a plurality of images obtained at different projection angles in the third modification of this embodiment.

In the second modification described above, the processing time in setting an ROI is shortened at the expense of the resolution of a 3D image. An ROI may be set on the basis of two or more images radiographed at different projection angles. FIG. 9 shows an apparatus arrangement for this operation.

Referring to FIG. 9, an aneurysm is radiographed from two directions first, and then the radiographic images are converted into digital signals by the A/D converter 2 and supplied to an ROI setting unit 21. In this case, if a biplane system having two pairs of X-ray tubes 12 and camera systems 13 is used, target images can be obtained by one radiographic operation.

The ROI setting unit 21 supplies the images to the displaying unit 8 through the D/A converter 9. If, for example, the frontal image. (Frontal) shown in FIG. 10A and the lateral image (Lateral) shown in FIG. 10B are displayed on the displaying unit 8, an ROI (center and radius) is set on each displayed image.

More specifically, a point K regarded as the center of an aneurysm is designated on one (in this case, for example, the frontal image) of the images (FIG. 10A). The ROI setting unit 21 computes a straight line (epipolar line) like the one indicated by the dotted line in FIG. 10B which connects the point K and the focus of the X-ray tube 12, and projects this line on the X-ray tube 12 on the opposite side (the lateral image side in this case). This projected straight line image is superimposed on the image.

Since the center of the aneurysm should be located on the epipolar line, a central point H shown in FIG. 10B is designated on this line. As in the above case, the ROI setting unit 21 computes a straight line that connects the point H and the focal point of the X-ray tube 12, and determines the intersection of the two straight lines as the central point of the ROI. These straight lines may not intersect. In such a case, the midpoint between the nearest points is obtained as the center of the ROI. A radius is designated on either the frontal image or the lateral image. An ROI is determined by correcting the radius in consideration of the geometrical magnification of X-rays.

When the ROI information is supplied from the ROI setting unit 21 to the collimater/bed controller 11, the collimater/bed controller 11 determines the aperture of the X-ray collimator 16 or the position of the bed or radiography system at an arbitrary projection angle on the basis of the ROI information.

More specifically, the bed or radiography unit 1 is moved to always locate the center of the ROI at the center of the camera system 13 during multiangle radiographic operation, as described with reference to FIG. 7. In addition, the X-ray collimator 16 is ON/OFF-controlled to irradiate only the ROI with X-rays. By radiographing only the ROI region, only the ROI is irradiated with X-rays even during multiangle radiographic operation before an occlusive material is detained. This makes it possible to reduce the excess dose of radiation to which the subject is exposed.

Second Embodiment

An X-ray diagnosis apparatus according to the second embodiment of the present invention will be described next. The same reference numerals as in the second embodiment denote the same parts in the first embodiment, and a description thereof will be omitted.

Figure 11:
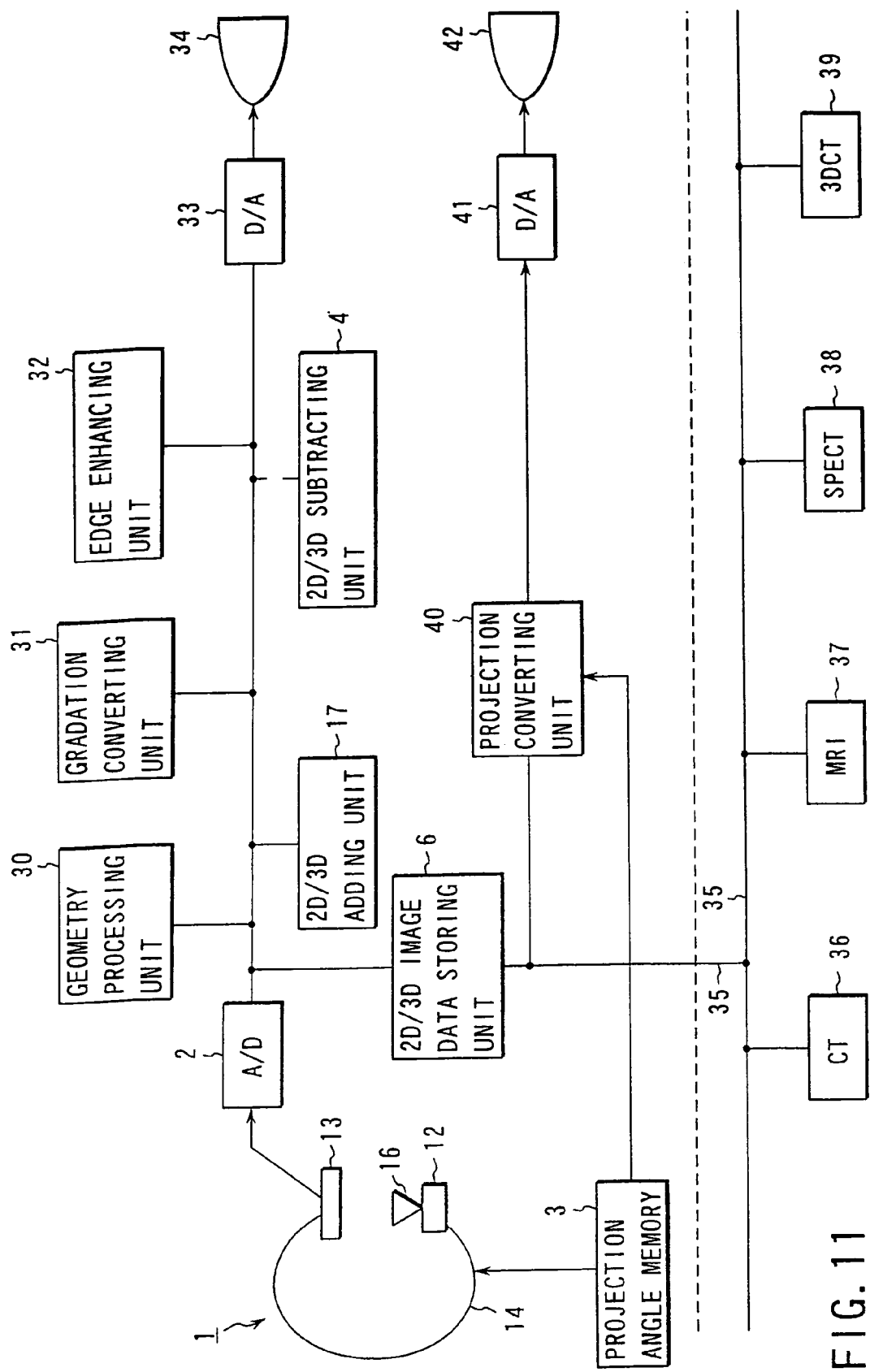
FIG. 11 is a block diagram showing the arrangement of an X-ray diagnosis apparatus for the circulatory system according to the second embodiment of the present invention.

As shown in FIG. 11, the X-ray diagnosis apparatus according to the second embodiment includes a radiography unit 1 for performing radiographic operation, an A/D converter 2 for digitizing a video signal supplied as analog information from the radiography unit 1, a memory 3 for storing radiographic conditions from the radiography unit 1, a geometry processing unit 30 for converting image data into a readable image, a gray-level converting unit 31, an edge enhancing unit 32, and a D/A converter 33 for converting the image data generated by these processing units 30, 31, and 32 into an analog signal to be displayed on a displaying unit 34.

The geometry processing unit 30 performs linear conversion for enlargement, rotation, movement, and the like. If a camera system 13 includes an image intensifier, the geometry processing unit 30 performs distortion correction processing.

The gray-level converting unit 31 adjusts display density to allow a target structure to be easily seen. The edge enhancing unit 32 performs edge emphasis processing by using a high-frequency emphasis filter (edge emphasis filter) such as a Laplacian or differential filter. The degree of each processing can be changed step by step by an input device (not shown), and each processing can be selectively executed.

The images acquired by the camera system 13 are A/D-converted by the A/D converter 2 and stored in an image data storing unit 6. In addition to the 2D images acquired by the X-ray diagnosis apparatus for the circulatory system, this image memory 6 stores the 3D images reconstructed by other modalities such as an X-ray CT apparatus 36, nuclear magnetic resonance apparatus 37 (MRI), and SPECT apparatus 38 connected to the X-ray diagnosis apparatus through a bus line 35, or the 3D images obtained by a 3D CT apparatus 39 such as an X-ray system for the circulatory system or similar system described in the first embodiment.

A projection converting unit 40 converts these 3D images into projection images at angles and positions coinciding with those of the currently radiographed image on the basis of the radiographic conditions supplied from the radiography unit 1 and recorded on the projection angle memory 3 in each radiographic operation. A D/A converter 41 converts these projection images into analog signals to be displayed on a displaying unit 42.

Although the second embodiment includes the two displaying units, i.e., the displaying unit 34 and displaying unit 42, this apparatus may include-one of these displaying units. In this case, radiographic and projection images are displayed to be juxtaposed or superimposed.

The operation of the second embodiment having this arrangement will be described next. In the second embodiment, first of all, the apparatus is operated while the operator moves a catheter to a morbid portion under fluoroscopic observation (radiographic operation with a low dose of radiation without injecting any contrast agent). In such a case, the operator cannot move the catheter forward unless he/she grasps blood vessel running. This is true especially when the blood vessel has a complicated structure. In general, therefore, before the operator moves the catheter forward, a contrast agent is injected to radiograph the blood vessel, and the contrast-enhanced image (still image) is displayed to be juxtaposed to the radiographed image (moving image: currently radiographed image) or superimposed thereon. With this operation, the operator can always grasp the blood vessel running without injecting any contrast agent. The examiner (operator) moves the catheter forward on the basis of the contrast-enhanced image (using the contrast-enhanced image as a guide). This contrast-enhanced image is called a road map. To generate a road map, however, radiographic operation must be performed with a contrast agent and a relatively large dose of radiation.

In the second embodiment, therefore, the projection converting unit 40 performs 3D projection conversion processing on the basis of a 3D image such as a CT image, MRI image, 3D image, or CT image which is obtained in advance by radiographing the same subject and the current radiographic conditions (SID, projection angle, radiographic mode, projection position, and the like). The resultant data is then provided as a road map through the D/A converter 41 and displaying unit 42. This projection conversion processing is performed every time the projection angle and position change. This makes it possible to reduce the amount of contrast agent and the dose of radiation which are used to generate a road map.

At this time, the projection converting unit 40 extracts a blood vessel portion from the CT image, MRI image, 3D image, CT image, or the like by threshold processing, and projects only the extracted blood vessel. If extraction is difficult to perform with a simple threshold, an interactive region-growing method may be used. Projection is performed while the values in the blood vessel which are extracted in this manner are replaced with arbitrary-absorption coefficients, and the absorption coefficients in other portions are set to 0, thereby generating a projection image like a DSA image. A CT image, 3D image, or CT image reconstructed from DSA image data is directly subjected to projection conversion.

A projection angle offset with respect to the patient due to the movement of the patient between acquisition of 3D images and catheter insertion can be corrected by using three or more markers reflected in the 3D image and radiographic images observed from two or more directions. Such a marker may be one that has a high absorption coefficient and pasted on the body surface or a characteristic structure inside the body, e.g., a branch of the blood vessel. More specifically, if three or more markers can be specified on the 3D image and radiographic images observed from two or more directions, the coordinates of the three markers within the coordinate system defined by the 3D image and the coordinates within the coordinate system defined by the radiography system can be calculated. The above correction can be performed by obtaining the rotational angle of the 3D image in which the three markers coincide with each other. Such operation of obtaining a correction angle may be performed once, before a road map is generated. In this case, although only the angles are made to coincide with each other, positions may also be made to coincide with each other.

Modification of Second Embodiment

In the second embodiment described above, a road map is generated every time the projection angle changes. In a region where a change in projection angle (translation) is small, a road map may be translated in accordance with a change in projection angle. In addition, in a region where a change in projection angle is small, since a change in load map with a change in angle is small as compared with a change in road map with position movement, a change in projection angle can be properly coped with to a certain degree without changing a road map. A road map is therefore computed and generated again only when the projection position or angle at which the previous road map was generated changes beyond a predetermined range. In a region where a change in projection position or angle is small, a change in projection angle can be properly coped with by the previous road map without generating any new road map.

Third Embodiment

An X-ray diagnosis apparatus according to the third embodiment of the present invention will be described next. The same reference numerals as in the first and second embodiments denote the same parts in the third embodiment, and a detailed description thereof will be omitted. When a road map is generated according to the procedure in the second embodiment, blood vessels overlap depending on the projection angle. This may make it difficult to identify a target blood vessel structure. The third embodiment is made to solve this problem.

Figure 12:
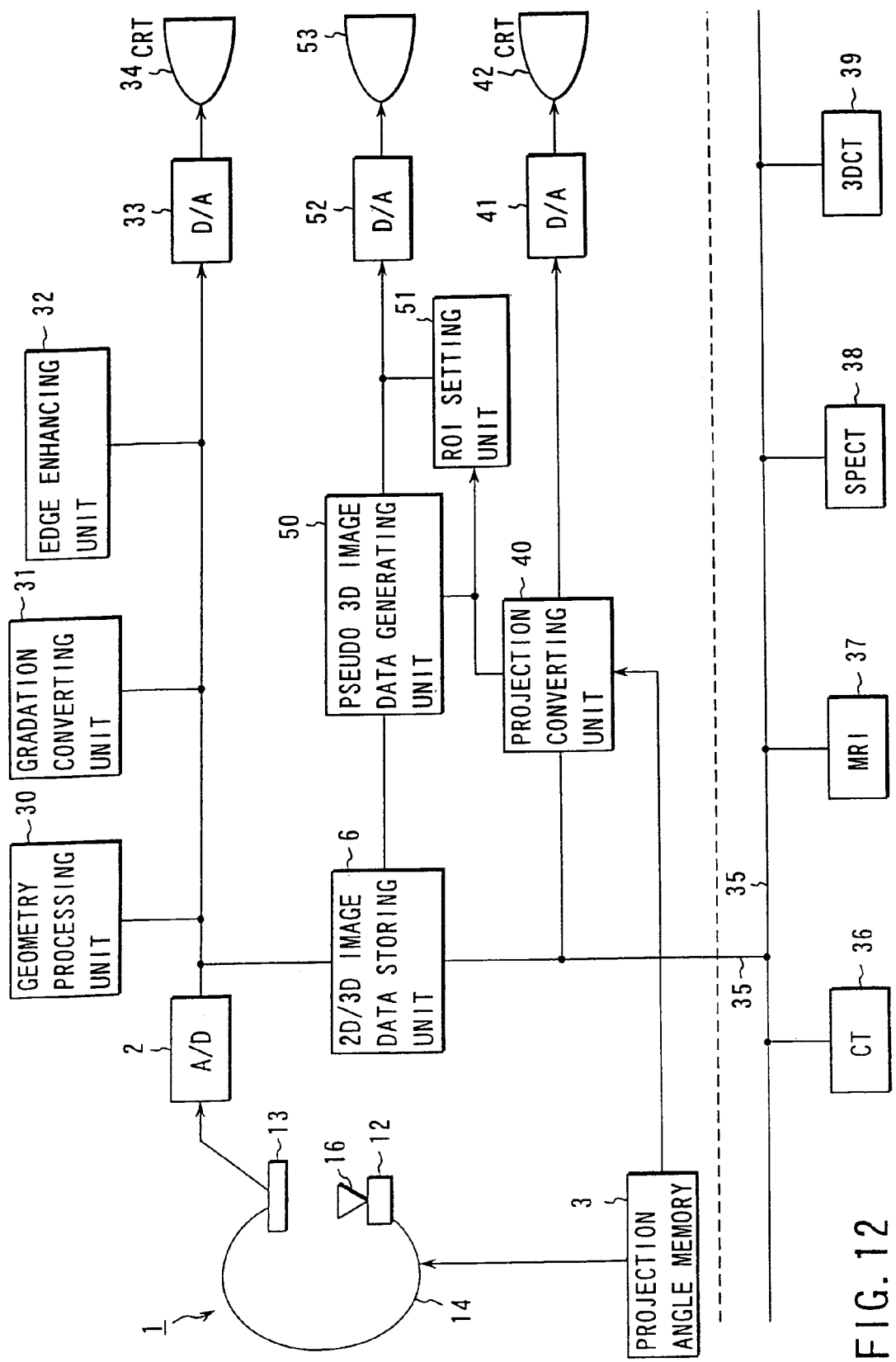
FIG. 12 is a block diagram showing the arrangement of an X-ray diagnosis apparatus for the circulatory system according to the third embodiment of the present invention.
Figure 13:
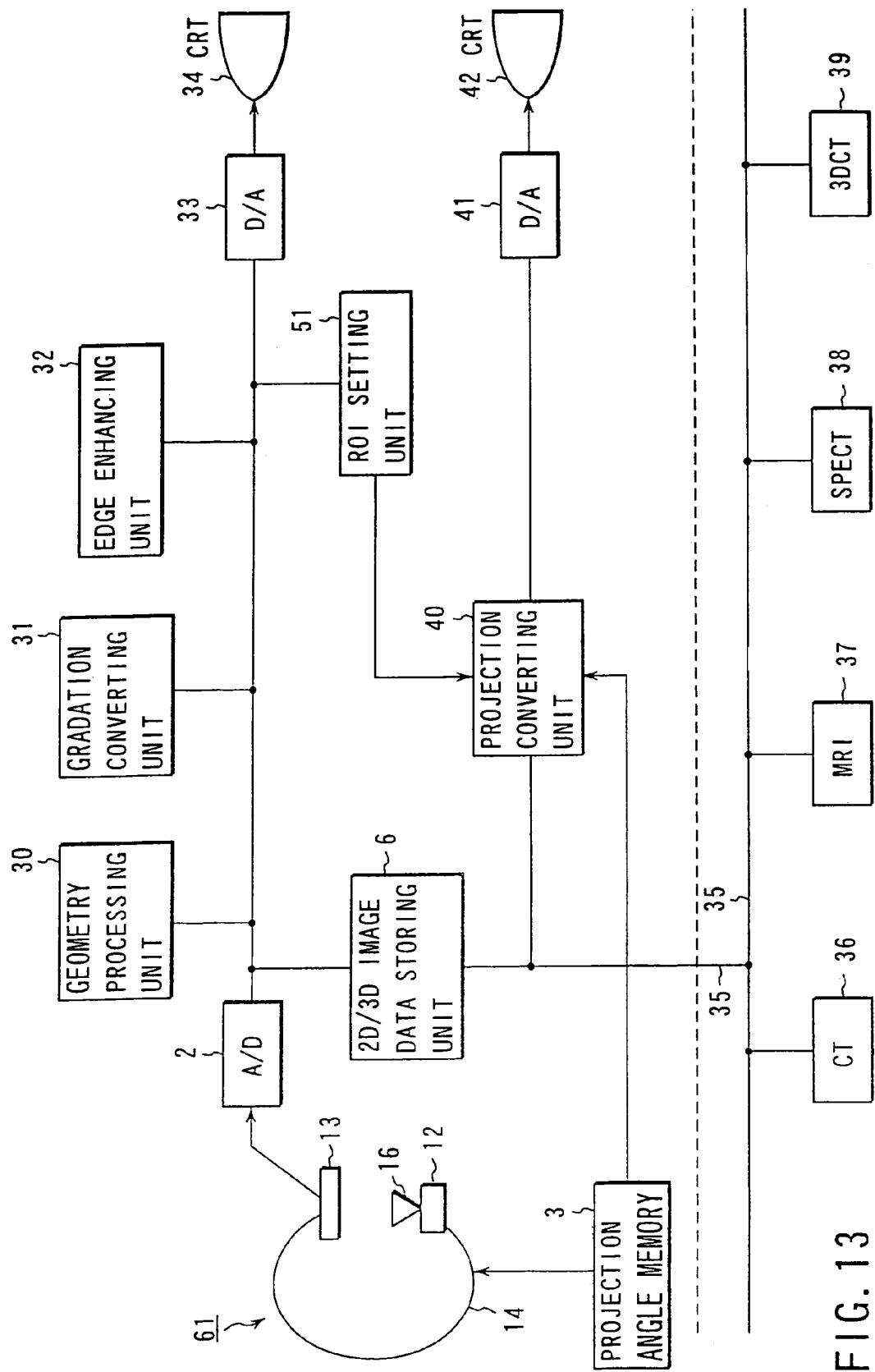
FIG. 13 is a block diagram showing the arrangement of an X-ray diagnosis apparatus having a biplane arrangement according to modifications of the third embodiment.

FIG. 12 shows the apparatus arrangement of the third embodiment, in which a pseudo 3D image data generating unit 50 extracts a target region from the 3D image data stored in an image memory 6 by the above simple threshold processing, region-growing method, or the like. The surface structure is then shaded. The resultant data is converted into an analog signal by D/A converter 52 to be displayed on a displaying unit 53. By observing this pseudo 3D image from various directions, the operator can grasp the 3D structure of the target region.

The operator then sets an ROI on this pseudo image using an ROI setting unit 51 in the same manner as in the first embodiment. When an ROI is set, the ROI setting unit 51 displays the ROI upon making it readable by changing the color of the internal portion of the ROI. In this case, the ROI is regarded as a spherical region. However, an ROI having a shape other than a spherical shape may be set. Alternatively, a plurality of ROIs may be designated. If a plurality of ROIs are designated, a final ROI is determined as an overlap of these ROIs.

The ROI information set by the ROI setting unit 51 is supplied to a projection converting unit 40. The projection converting unit 40 calculates a projection image on the basis of the ROI information such that data other than that in the ROI is not projected on a projection region corresponding to the ROI, and displays the projection image on a displaying unit 42 through a D/A converter 41.

Alternatively, the projection converting unit 40 clarifies a projection image in the ROI by weakening data other than that in the ROI by using weighting factors in a region where the ROI is radiographed, and displays the resultant image on the displaying unit 42.

In this manner, a blood vessel structure that is difficult to specify because images overlap on a road map can be easily specified by omitting display of blood vessel structure images overlapping each other on the road map or weakening its display. Therefore, the operator can quickly move the catheter forward. This makes it possible to shorten the examination (therapy) time and reduce the dose of radiation.

First Modification of Third Embodiment

In the third embodiment, an ROI is manually designated. This modification uses a biplane type unit capable of observation from two directions as a radiography unit 61. With this unit, 3D position coordinates at which a catheter exists may be calculated on the basis of the image coordinates of the distal end of the catheter, which is a characteristic structure extracted from images in two directions, and an ROI centered on the calculated point may be set. As a technique of extracting an image of the distal end of the catheter, a technique of detecting a material having a high absorption coefficient and attached to the distal end of the catheter, a technique of extracting a portion corresponding to a time difference, or the like can be used. This makes it possible to automatically set an ROI.

Second Modification of Third Embodiment

In the first modification of the third embodiment, an ROI is automatically set by using the radiography unit 61 having the biplane arrangement. However, an ROI can also be automatically set by using a single-plane X-ray diagnosis apparatus in the same manner as described above.

In this case, the distal end of a catheter is specified on a radiographic image, and the image is back projected from the specified point within the image coordinate system. At this time, a blood vessel structure that intersects a backprojection line is set as a candidate for the center of an ROI.

More specifically, a density distribution is searched along the backprojection line, and a point at which the detected density exceeds the density of the blood vessel first and a point at which the detected density becomes lower than the density of the blood vessel next are recognized as points defining a boundary of one blood vessel structure. The midpoint between the detected points is then set as a candidate point of the ROI. This operation is repeated on the line to obtain a plurality of candidate points. A similar search is made along a line segment connecting each candidate point and the center of the ROI in a frame one or a plurality of frames ahead of the current frame. If a region other than the blood vessel enters the search area, the corresponding candidate point is canceled. The number of candidate points can be decreased by the above operation. In some case, a candidate point cannot be uniquely specified by this method. In such a case, a plurality of ROIs are set. The operator selects a desired ROI from the plurality of designated ROIs. This makes it possible to semi-automatically set an ROI even by using a single-plane X-ray diagnosis apparatus.

Third Modification of Third Embodiment

In the third embodiment described above, the density of a 3D blood vessel image is projected. However, the distance from the X-ray focal point or the detector to the surface of a target region may be projected. In this case, since pieces of projected information always overlap, only information having the smallest or largest value is projected. With this operation, depth information can be added to a 2D road map, and hence catheter operation is facilitated. This makes it possible to shorten the examination time and reduce the dose of radiation.

Fourth Modification of Third Embodiment

In the third modification of the third embodiment, the distance from the boundary of a target region to an X-ray tube 12 or camera system 13 is projected and displayed. However, this image may be displayed in color and color bar. In addition, depth information at the position of the ROI in the color bar may be displayed more clearly by displaying an arrow or the like.

Fifth Modification of Third Embodiment

In the third and fourth modifications of the third embodiment, the distance from the boundary of a target region to the X-ray tube 12 or camera system 13 is projected and displayed. However, the display density or color may be updated around the current position. For example, the display colors are dynamically changed such that the current position is always displayed in the central color of the color bar. However, incessant changes in color make it difficult to grasp the structure of a portion whose depth greatly changes. Alternatively, therefore, the color may be changed on the basis of one or a combination of some of the following conditions: predetermined time intervals, a predetermined change in depth, a change in projection angle, and a change in projection position. A reset switch or the like may be used to change the color upon depression of the switch. This makes it possible to display depth information near an ROI more clearly.

Sixth Modification of Third Embodiment

In the third, fourth, and fifth modifications of the third embodiment, distance information about an overall blood vessel structure (including the axis and other portions) is projected. However, depth information is only required to indicate the central axis. For this reason, only the central axis of the blood vessel is extracted first from a 3D image by a thinning method, and only the extracted central line is projected as distance information, while density information is projected for other portions. Note that 3D thinning processing can be basically performed by extension from 2D to 3D. This makes it possible to simultaneously observe a conventional road map and depth information. This therefore can provide depth information while preventing confusion of the operator (examiner). Making the projected central line relatively thick will make the displayed image more readable.

The density information of the projected central line may be set as the boundary of the blood vessel. If this information is displayed on the axis of the blood vessel, the information is difficult to reach depending on the density of the road map. However, setting the information at the boundary of the blood vessel makes it more readable. This processing can be executed by thinning the road map, making the resultant data correspond to the projected central line, and finding two nearest boundaries in a direction perpendicular to the thinned central line.

The present invention is not limited to the above embodiments. Various changes and modifications of the present invention other than the respective embodiments can be made in accordance with design and the like within the technical scope of the invention.

In each embodiment described above, the coil (occlusive material) is detained. This is an example presented to facilitate the understanding of the present invention. Note that the present invention is effective before and after a change of every circumstance as well as these therapies and the like.

Additional advantages and modifications will readily occur to those skilled in the art. Therefore, the invention in its broader aspects is not limited to the specific details and representative embodiments shown and described herein. Accordingly, various. modifications may be made without departing from the spirit or scope of the general inventive concept as defined by the appended claims and their equivalents.

What is claimed is:

1. An X-ray diagnosis apparatus, comprising:
   a radiography unit including
      an arcuated arm having an X-ray tube mounted at one end of the arcuated arm;
      the X-ray tube configured to irradiate a subject with an X-ray during a scan that includes a plurality of projection angles;
      a camera system configured to detect an X-ray transmitted through the subject; and
      a collimator arranged between said X-ray tube and said X-ray detection unit and configured to variably limit an irradiation field in which the subject is irradiated with the X-ray;
   an image data generating unit configured to generate at least one of 2D and 3D image data based on an output from said X-ray detection unit;
   a displaying unit that displays the 3D image data;
   an ROI setting unit configured to set a region of interest on the displayed 3D image in accordance with a user instruction;
   a mechanism configured to move said radiography unit, including rotating the arcuated arm; and
   a controller configured to control said collimator based on a position and a size of the set region of interest so as to adjust the irradiation field to a range corresponding to the set region of interest, and to control said mechanism based on the position and the size of the set region of interest,
   wherein said controller controls said collimator during the scan in accordance with a rotation of the arcuated arm so as to position a center of the set region of interest at a center of the camera system of the X-ray diagnosis apparatus at each of the projection angles in the scan; and
   wherein said controller controls an aperture of said collimator for each of the plurality of projection angles in the scan so that only the set region of interest is irradiated at each of the plurality of projection angles in the scan.

2. An X-ray diagnosis apparatus, comprising:

a radiography unit including an arcuated arm having an X-ray tube mounted at one end of the arcuated arm;

the X-ray tube configured to irradiate a subject with an X-ray during a scan that includes a plurality of projection angles;

an X-ray detection unit configured to detect an X-ray transmitted through the subject; and a collimator arranged between said X-ray tube and said X-ray detection unit and configured to variably limit an irradiation field in which the subject is irradiated with the X-ray;

an image data generating unit configured to generate at least one of 2D and 3D image data based on an output from said X-ray detection unit;

a displaying unit that displays the 3D image data;

an ROI setting unit configured to set a region of interest on the displayed 3D image in accordance with a user instruction;

a mechanism configured to move said radiography unit, including rotating the arcuated arm; and a controller configured to control said collimator based on a position and a size of the set region of interest so as to adjust the irradiation field to a range corresponding to the set region of interest, and to control said mechanism based on the position and the size of the set region of interest, wherein said controller controls said collimator during the scan in accordance with a rotation of the arcuated arm, based on a center and a radius of the set region of interest; and wherein said controller controls an aperture of said collimator for each of the plurality of projection angles in the scan so that only the set region of interest is irradiated at each of the plurality of projection angles in the scan.

* * * * *